United States Patent [19]

Schirmann et al.

[11] 4,303,587

[45] Dec. 1, 1981

[54] CATALYTIC EPOXIDATION OF OLEFINS

[75] Inventors: Jean-Pierre Schirmann, Oullins; Serge Y. Delavarenne, Francheville le Haut, both of France

[73] Assignee: Produits Chimiques Ugine Kuhlmann, Courbevoie, France

[21] Appl. No.: 73,440

[22] Filed: Sep. 7, 1979

Related U.S. Application Data

[63] Continuation of Ser. No. 872,947, Jan. 27, 1978, abandoned.

[30] Foreign Application Priority Data

Feb. 1, 1977 [FR] France ............................... 77 02748
Oct. 28, 1977 [FR] France ............................... 77 32584

[51] Int. Cl.³ ........................................... C07D 301/12
[52] U.S. Cl. ............................................... 260/348.31
[58] Field of Search ..................................... 260/348.31

[56] References Cited

U.S. PATENT DOCUMENTS

| | | | |
|---|---|---|---|
| 2,833,788 | 5/1958 | Skinner et al. | 260/348.31 |
| 3,293,269 | 12/1966 | Wolgemuth | 260/348.31 |
| 3,518,285 | 6/1970 | Fenton et al. | 260/348.31 |
| 3,597,459 | 8/1971 | Mimoun et al. | 260/348.31 |
| 3,708,506 | 1/1973 | Brunie et al. | 260/348.29 |
| 3,716,563 | 2/1973 | Brunie et al. | 260/348.24 |
| 3,806,467 | 4/1974 | Watanabe et al. | 252/429 |
| 3,832,363 | 8/1974 | Fetterly et al. | 260/348.29 |

FOREIGN PATENT DOCUMENTS 868890  5/1961  United Kingdom ........... 260/348.27

OTHER PUBLICATIONS

Wolf et al., Jour. Org. Chem., vol. 34, No. 11, Nov. 1969, pp. 3441–3445.
Chemical Abstracts, vol. 66 (1967) 77863d.
Daniel Swern, Organic Peroxides, vol. I (1970) pp. 50–51.

*Primary Examiner*—Norma S. Milestone
*Attorney, Agent, or Firm*—Pennie & Edmonds

[57] ABSTRACT

The invention disclosed provides a method for the direct epoxidation of olefins in the liquid phase by reacting the olefin with hydrogen peroxide in the presence of a boron containing catalyst while continuously removing water from the reaction mixture.

15 Claims, No Drawings

CATALYTIC EPOXIDATION OF OLEFINS

This is a continuation of application Ser. No. 872,947, filed Jan. 27, 1978, now abandoned.

BACKGROUND OF THE INVENTION

1. Field of the Invention

The present invention relates to a method for the direct epoxidation of olefins in the liquid phase by reacting the olefin with hydrogen peroxide at a temperature between 0° C. and 120° C. in the presence of a boron containing catalyst while continuously eliminating the water introduced with the hydrogen peroxide as well as the water formed in the course of the reaction by distillation, or azeotropic distillation, or entrainment or by combination with a reagent susceptible to react with water in the reaction conditions.

2. Description of the Prior Art

Epoxidated olefins are important commercially and are used in great quantities as intermediates in the manufacture of urethanes, glycols, surfactants, plasticizers, and the like. However, processes available to the art for the epoxidation of olefins are becoming less and less suitable because they are subject to ecology restrictions while also being uneconomical.

It is well known that the chlorohydrin process, for example, wherein an olefin is reacted with chlorine in an alkaline medium, is unsatisfactory because producing considerable amounts of inorganic and organic chlorinated by-products which are difficult to dispose of and which have limited practical usage.

Another process known to the art which involves lesser pollutants is based on the catalytic epoxidation of an olefin in an anhydrous medium by means of an organic hydroperoxide resulting from the oxidation of a saturated hydrocarbon with molecular oxygen. Production of the epoxide is accompanied, however, by production of at least an equivalent quantity of the alcohol corresponding to the starting hydroperoxide. Production of the latter product presents a problem since it considerably influences the economy of the process.

Because of the inherent disadvantages in prior art processes for catalytic epoxidation of olefins, the industry continues to seek more direct methods for epoxidation of olefins, as well as methods which have a higher yield to avoid the problem of by-products.

Direct epoxidation of olefins by molecular oxygen has been the subject of numerous investigations. Thus far, however, this process has been limitedly used in epoxidation of ethylene with good yields using a silver base catalyst. When this technique is used on other olefins, there is a total lack of selectivity.

Hydrogen peroxide is a useful reactant because of its nature as a non-polluting oxidizing agent. However, its reactivity as an epoxidizing agent in regard to unactivated olefins is low and requires the presence of an activating agent to produce, in situ, a more active percompound. There have been proposed various epoxidation processes using, for example, peracids such as performic, peracetic or perpropionic acid, such as that disclosed in Belgian Pat. No. 838,068. However, because of the instability of epoxides in an acid medium, such processes are particularly difficult to use.

Various catalytic processes have also been described in the art which have the advantage over the above processes of not using stoichiometric quantities of percompounds whose synthesis complicates the process of obtaining epoxides. For example, there has been proposed the use, in an aqueous or water-alcohol medium, of oxides or oxyacids derived from transition metals such as molybdenum, tungsten, vanadium, titanium, and the like. These processes are not satisfactory because the desired epoxide is not obtained, but instead the corresponding glycol or mixtures of products resulting from the opening of the oxirane cycle.

The use of peroxide complexes of some of these transition metals has also been proposed such as the technique described in French Pat. No. 2,082,811. These complexes are good epoxidazing agents but their in situ regeneration presents such a problem that industrial application of the process is not feasible.

Belgian Pat. No. 747,316 discloses the use of hydrogen peroxide as an epoxidizing agent in the presence of a catalyst on a base of an organic derivative of tin. It is difficult, however, to utilize this process on an industrial scale.

In French Pat. No. 2,245,582 there is described a process for the epoxidation of an olefin by means of hydrogen peroxide in the presence of a catalytic system containing at least one derivative of lead and at least one derivative of the elements of Groups IVA, VA, VIA of the Mendeleev Periodic Table.

In French Pat. No. 2,300,765 applicants have described the use of various organic and mineral derivatives of arsenic in conjunction with a derivative of a transition metal belonging to Groups IVA, VA and VIA of the Periodic Table as catalysts for epoxidation of olefins by hydrogen peroxide in liquid phase. Also, there is a more recent proposal in Belgian Pat. No. 838,953 of a method for making oxides of olefins by action of hydrogen peroxide on olefins in the presence of an organic or mineral derivative of arsenic and in the absence of any trace of transition metal. However, in order to obtain good yields, these methods require the use of highly concentrated aqueous solutions of hydrogen peroxide which are not commercially available at present, and the manufacture and handling of which involves serious problems of safety. These major drawbacks are supplemented by the defect of an epoxidation reaction that is certainly effective but very slow and is difficult to economically scale to an industrial production unit.

It has now been found during continuing study of the epoxidation of olefins, that it is easily possible to overcome numerous prior art drawbacks by operating a method for production of olefins by using a boron containing catalyst and a substantial excess of olefin relative to hydrogen peroxide and by continuously eliminating from the reaction medium the water formed in the course of the reaction as well as any water introduced with the hydrogen peroxide either by direct distillation or by azeotropic distillation or by simple entrainment procedures or by combination with a reagent susceptible to react with water in the reaction conditions. Under these conditions, it is found that rates of conversion of the hydrogen peroxide and epoxide selectivities are very high, simply by using commercial aqueous solutions titrating between 30% and 70% by weight of hydrogen peroxide. Furthermore, the boron catalyst is found to have a long life and thereby avoids frequent replacement.

SUMMARY OF THE INVENTION

The present invention relates to a method of epoxidation of olefins in liquid phase by action of hydrogen peroxide in the presence of a boron containing catalyst according to the reaction:

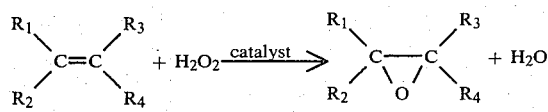

in which $R_1$, $R_2$, $R_3$ and $R_4$ are identical or different and represent either a hydrogen atom, a straight alkyl radical having from 1 to 30 carbon atoms, a branched alkyl radical or cycloalkyl radical, either substituted or unsubstituted and having from 3 to 12 carbon atoms, a hydrocarbon radical haing from 6 to 12 carbon atoms and containing a phenyl group which may be substituted or unsubstituted by alkyl groups; $R_1$ and $R_2$ or $R_3$ and $R_4$ together may also represent a straight or branched alkylene group having from 2 to 11 carbon atoms or $R_1$ and $R_3$ or $R_2$ and $R_4$ together may represent a linear or branched alkylene group having from 1 to 10 carbon atoms. The radicals $R_1$, $R_2$, $R_3$ and $R_4$ can be unsaturated and/or substituted with functional groups which are stable in the reaction medium, such as hydroxy, chloro, fluoro, bromo, iodo, nitro, nitroso, alkoxy, amino, carbonyl, alkylcarbonyl carboxylic acid, carboxylic acid ester, amide or carbamyl, nitrile or cyano and the like. These members may be also unsaturated, i.e., including polyolefins such as the dienes, trienes, and the like, either conjugated or unconjugated by effecting reaction in the presence of a substantial excess of olefins relative to the hydrogen peroxide, and in eliminating the water formed in the course of the reaction, as well as that which may be introduced with the hydrogen peroxide continuously, such as by distillation, azeotropic distillation or entrainment or combination with a reagent susceptible to react with water in the reaction conditions.

DETAILED DESCRIPTION OF THE INVENTION

The present invention relates to a method of epoxidation of olefins in liquid phase by action of hydrogen peroxide in the presence of a boron containing catalyst according to the reaction:

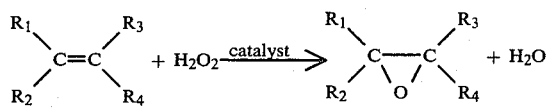

in which $R_1$, $R_2$, $R_3$ and $R_4$ are identical or different and represent either a hydrogen atom, a straight alkyl radical having from 1 to 30 carbon atoms, a branched alkyl radical or cycloalkyl radical, either substituted or unsubstituted and having from 3 to 12 carbon atoms, a hydrocarbon radical having from 6 to 12 carbon atoms and containing a phenyl group which may be substituted or unsubstituted by alkyl groups; $R_1$ and $R_2$ or $R_3$ and $R_4$ together may also represent a straight or branched alkylene group having from 3 to 11 carbon atoms; or $R_1$ and $R_3$ or $R_2$ and $R_4$ together may represent a linear or branched alkylene group having from 1 to 10 carbon atoms. The radicals $R_1$, $R_2$, $R_3$ and $R_4$ can be unsaturated and/or substituted with functional groups which are stable in the reaction medium, such as hydroxy, chloro, fluoro, bromo, iodo, nitro, nitroso, alkoxy, amino, carbonyl, alkylcarbonyl carboxylic acid, carboxylic acid ester, amide or carbamyl, nitrile or cyano and the like. These members may be also unsaturated, i.e., including polyolefins such as the dienes, trienes, and the like, either conjugated or unconjugated, by effecting reaction in the presence of a substantial excess of olefins relative to the hydrogen peroxide, and in eliminating the water formed in the course of the reaction, as well as that which may be introduced with the hydrogen peroxide, continuously such as by distillation, azeotropic distillation or entrainment or by combination with a reagent susceptible to react with water in the reaction conditions.

The unsaturated compounds which can be epoxidized by the process according to the invention comprise, by way of nonlimiting examples, ethylene, propylene, butenes, butadiene, pentenes, hexene-1, hexene-3, heptene-1, octene-1, diisobutylene, nonene-1, limonene, pinene, myrcene, camphene, undecene-1, dodecene-1, tridecene-1, tetradecene-1, pentadecene-1, hexadecene-1, heptadecene-1, octadecene-1, nonadecene-1, eicosene-1, trimers and tetramers of propylene, polybutadienes, styrene, alpha-methyl styrene, divinyl benzene, indene, stilbene, cyclopentene, cyclohexene, cycloheptene, cyclooctene, cyclooctadiene, cyclododecene, cyclododecatriene, dicyclopentadiene, methylenecyclopropane, methylenecyclopentane, methylenecyclohexane, vinylcyclohexene, methylallylketone, allyl chloride, allyl bromide, acrylic acid, methacrylic acid, crotonic acid, vinyl acetic acid, crotyl chloride, methallyl chloride, dichlorobutenes, allyl alcohol, allyl carbonate, allyl acetate, alkyl acrylates and methacrylates, diallyl maleate, diallyl phthalate, unsaturated oils such as soya oil, sunflower oil, corn oil, cottonseed oil, olive oil, ricinus oil, codliver oil, peanut oil, tall oil, linseed oil, unsaturated fatty acids such as oleic, linoleic, balidic, erucic, oleostearic, myristoleic, palmitoleic, licanic ricinoleic, arachidonic acids, and the like, as well as their esters.

The catalyst which is used in the present method may be either elementary boron, a mineral or organic derivative of boron, or a mixture of two or more of these compounds.

The boron catalyst is introduced into the reaction system in any economically available form, such as, for example, in the form of boron trioxide, or boric acid and, generally speaking, in any form which can be transformed, in situ, under the conditions of the present reaction, into a catalytically active boron compound.

The following non-limiting examples are boron compounds useful herein: boron oxides $B_2O_2$, $B_2O_3$ and $B_4O_5$, boron oxyacids, such as orthoboric acid $H_3BO_3$, metaboric acid $(HBO_2)_3$, tetraboric acid $H_2B_4O_7$ and their esters, heteropolyacids such as borotungstic acid, boron halides, and the like. Esters of boron oxyacids, which can be considered as a combination of inorganic and organic derivatives, can also serve as a reaction medium in which the olefin is dissolved to achieve the epoxidation reaction. In this case, the ester acts both as solvent and catalyst.

According to the method of the invention, it is desirable that the reaction medium be such that the olefin and the solution of hydrogen peroxide be entirely miscible under the reaction conditions. In other words, the system according to the invention must have only one single liquid phase. Furthermore, this medium must be as inert as possible with respect to the reagents and the epoxide formed. The reaction can be embodied in certain cases by bringing the reagents, i.e., the olefin and hydrogen peroxide, in contact in the absence of a solvent. It is then necessary to operate with a molar ratio of olefin to $H_2O_2$ that is high enough, for obvious reasons of safety, and, more particularly, comprised between 2 and 200. It is preferred to operate in the present method in an inert, organic solvent or a mixture of solvents, such as, for example, primary, secondary, or tertiary alcohols having from 1 to 6 carbon atoms, such as methanol, ethanol, n-propanol, isopropanol, butanol-1, butanol-2, tertiary butanol, amyl alcohol, isoamyl alcohol, tertiary amyl alcohol, cyclohexanol, ethylene glycol, propylene glycol, glycerol, and the like; oxide ethers, such as ethyl ether, isopropyl ether, dioxane, tetrahydrofurane; the oligomers of ethylene oxide, propylene oxide, or their ethers, such as dimethoxy-diethylene glycol, diethoxy-ethylene glycol, diglyme, and the like; or esters, especially the formates, acetates or propionates of the usual alcohols or glycols. Other appropriate solvents which may be used include dimethylformamide, nitromethane, the triethyl, trioctyl and ethylhexyl phosphates, and the like.

The preferred method for epoxidizing the olefin compounds according to the process of the invention consists in reacting the hydrogen peroxide and the olefin in the presence of the catalyst and a solvent in conditions which allow the elimination of the water introduced by the hydrogen peroxide as well as the water formed in the course of the reaction. The temperature at which the reaction takes place is between 0° C. and 120° C. and preferably between 70° C. and 100° C. According to the temperature selected and the reaction system used, i.e., olefin and solvent, the reaction can be accomplished by operating at reduced pressure or at atmospheric pressure. Alternatively, the reaction can be effected under pressure when the temperature is about 100° C., in particular, when light olefins are processed. The pressure can, therefore, vary between 20 mm. of mercury and 100 bars, if necessary.

If the elimination of the water is to be achieved by distillation, it can be accomplished by simple distillation if the boiling points of the olefin, the solvent and the epoxide permit such distillation to be effected. It is also possible to use azeotropic distillation either by reason that an azeotrope is formed between the water and the olefin or by incorporating, in the medium, a co-solvent having azeotropic properties. Examples of useful co-solvents include benzene, toluene, n-pentane, cyclohexane, and anisole. Also, it is possible to entrain the water, because the vapor pressure at a given temperature by continuous passage of a gas into the reaction medium. This gas can be the olefin when light olefins are processed.

The choice of reaction temperature depends, naturally, on the stability of the hydrogen peroxide in the reaction medium selected.

The reaction time depends on the nature of the catalyst used, on the solvent and on the particular olefin. The reaction time can vary from a few minutes to 100 hours and, if necessary, more. The reagents can also be used in equimolecular amounts and in varying proportions. Preferably, the olefins are used in excess relative to the amount of hydrogen peroxide. It is possible to use from 0.1 to 50 moles of olefin per mole or hydrogen peroxide, and preferably about from 1 to 10 moles.

The catalyst is used at the rate of 0.0001 to 1 mole of boron per mole of hydrogen peroxide. Preferably, a molar ratio between 0.001 and 0.1 mole of catalyst per mole of hydrogen peroxide is used.

The amount of solvent or mixture of solvents is determined by the quantity necessary to maintain a single liquid phase and avoid any phenomena of unmixing. The amount of solvent usually is between 25% and 55% of the total volume of the reaction medium.

The reagents can be used in commercially available form. The hydrogen peroxide, in particular, can be used in the form of commercial aqueous solutions, which contain from 30% to 70% by weight of hydrogen peroxide. In view of the fact that the method of the present invention involves a continuous elimination of the water present in the reaction medium, it will be apparent that the use of aqueous solutions of hydrogen peroxide containing more than 70% by weight of hydrogen peroxide and, in particular, from 85% to 95% by weight of hydrogen peroxide is possible. It is preferable to predissolve the concentrated hydrogen peroxide in the solvent serving as reaction medium and, thus, to use dilute organic solutions for obvious reasons of safety.

Another particularly interesting embodiment of the process according to the invention consists in putting in contact, in liquid phase, an olefin, hydrogen peroxide and an inorganic or organic derivative of boron which is able to play the role of a catalyst or to generate such a catalyst and in the same time to fix the water of the reaction medium, the boron catalyst being selected, in particular, from the group consisting of boric oxide $B_2O_3$, metaboric acid $(HBO_2)_3$, tetraboric acid, metaboric esters, orthoboric esters, in a solvent as defined previously thereby making a miscible olefin and hydrogen peroxide system possible. The temperature at which the reaction is performed is between 0° C. and 120° C. and, preferably, between 70° C. and 100° C. Depending on the nature of the olefin used and the temperature selected, the pressure can vary between 1 and 100 bars, if necessary. The boron compound is used at the rate of 0.5 to 10 moles per mole of hydrogen peroxide. This embodiment is particularly useful for epoxidation of light olefins such as ethylene, propylene, butenes. Obviously this embodiment cn be combined with the elimination of water by distillation, azeotropic distillation or entrainment.

Practice of the present invention will become more apparent from the non-limiting examples following wherein all parts are by weight unless otherwise indicated and wherein the selectivity is defined as being the number of moles of epoxides formed relative to the number of moles of reacted hydrogen peroxide.

EXAMPLE 1

In a 300 cc. glass reactor equipped with a mechanical stirrer and a reflux condenser equipped with a Florence flask, are placed 47 g. of diethyleneglycol dimethyl ether ($CH_3$—$OCH_2$—$CH_2$—O—$CH_2$—$CH_2$—O—$CH_3$), 82 g. of cyclohexene (1 mole) and 0.2 g. of boric oxide $B_2O_3$ (0.03 mole). The system is brought to reflux, after which 2.36 g of a 70% hydrogen peroxide solution (0.0485 mole) dissolved in 20 g. of diethyleneglycol dimethyl ether, are introduced over one-half hour period of time. The water is continually eliminated from the reaction mixture by azeotropic distillation with cyclohexene. After an hour of reaction, the reaction mixture is found to contain 1.3 millimole of unreacted hydrogen peroxide and 0.041 mole of cyclohexene epoxide whereas 5.2 millimoles of $H_2O_2$ is found in the distillate. This corresponds to a selectivity of 97.6% for a conversion of 86.6%.

EXAMPLE 2

In a 500 cc. glass reactor equipped with a mechanical stirrer and a reflux condenser equipped with a Florence flask, are placed 82 g. of cyclohexene (1 mole), 25 g. of cyclohexanol (0.25 mole) and 8.7 g. of boron trioxide (0.125 mole). The system is brought to boiling while continually eliminating the water by azeotropic distillation. After 3 hours of reaction, the boric oxide is completely dissolved and there is obtained a clear solution of cyclohexyl metaborate in cyclohexene. To this solution, are added under reflux conditions and over 90 minutes, 70 millimoles of hydrogen peroxide in the form of a 70% aqueous solution by weight. After completion of the addition, the reaction medium is found to contain 16 millimoles of cyclohexene epoxide, which corresponds to a selectivity of 23% for a conversion rate of 95%.

EXAMPLE 3

In a glass reactor equipped with mechanical stirrer and a reflux condenser are placed 82 g. of cyclohexene (1 mole), 52 g. of dioxane and a 0.2 g. of boron trioxide $B_2O_3$ (0.05 mole). This mixture is brought to reflux, and there is then added over 30 minutes, a 2.6 g. solution of 70% hydrogen peroxide (0.055 mole) in 20 g. of dioxane. The water is eliminated from the reaction mixture continually by azeotropic distillation with cyclohexene. After one hour of reaction, the reaction medium is found to contain 0.005 mole of unreacted hydrogen peroxide and 4.99 g. of cyclohexene epoxide (0.050 mole) which corresponds to a selectivity of 100% for a conversion rate of hydrogen peroxide of 91%.

EXAMPLE 4

Example 3 is repeated except that boron trioxide is replaced with 0.2 g. of orthoboric acid $H_3BO_3$ (0.03 mole). After 90 minutes of reaction, the reaction medium is found to contain 0.001 mole of unreacted hydrogen peroxide and 5.2 g. of cyclohexene epoxide (0.053 mole) which corresponds to a 98% selectivity for a 98% hydrogen peroxide conversion rate.

EXAMPLE 5

Example 3 is repeated except that boron trioxide is replaced with 0.2 g. of cyclohexyl metaborate (0.0015 mole). There is introduced over one hour, a solution of 7.8 g. of a 70% hydrogen peroxide (0.154 mole) in 50 g. of dioxane. After 2 hours of reaction, the reaction medium is found to contain 0.067 mole of unreacted hydrogen peroxide and 6.96 g. of cyclohexene epoxide (0.071 mole), which corresponds to an 81.6% selectivity for a conversion rate of hydrogen peroxide of 56.5%.

EXAMPLE 6

Example 3 is repeated except that dioxane is replaced by 50 g. of ethylene glycol diacetate. After one hour of reaction, the reaction medium is found to contain 0.002 mole of unreacted hydrogen peroxide and 3.9 g. of cyclohexene epoxide (0.040 mole) which corresponds to a 75.5% selectivity for a conversion rate of hydrogen peroxide of 96.4%.

EXAMPLE 7

In a 250 cc. reaction flask equipped with a mechanical stirrer are placed 82 g. of cyclohexene (1 mole), 60 g. of diethyleneglycol dimethyl ether, i.e., diglyme, ($CH_3$—O—$CH_2$—$CH_2$—O—$CH_2$—$CH_2$—$OCH_3$) and 2.1 g. of boric oxide $B_2O_3$ (0.03 mole). The medium is brought to 91° C. at there are then introduced over 15 minutes, 22 g. of an anhydrous solution of hydrogen peroxide in diglyme (0.051 mole). After two hours of reaction, the reaction medium is found to contain 0.006 mole of hydrogen peroxide and 0.043 mole of cyclohexene epoxide. This corresponds to a conversion rate of $H_2O_2$ of 89% for a selectivity of 93%.

EXAMPLE 8

In a 250 cc. glass reactor equipped with a mechanical stirrer are placed 82 g. of cyclohexene (1 mole), 40 g. of diglyme, and 0.3 mole of 1,2-propanediol orthoborate prepared from 0.3 mole of orthoboric acid and 0.45 mole of 1,2-propanediol. This mixture is brought to 85° C. and there are then introduced 3.16 g. of 70% hydrogen peroxide (0.064 mole). After 1 hour 30 minutes reaction time, the reaction medium is found to contain 0.008 mole of $H_2O_2$ and 0.054 mole of cyclohexene epoxide. This corresponds to a conversion rate of $H_2O_2$ of 87% for a 97% selectivity.

EXAMPLE 9

The procedure of Example 8 is repeated except that the cyclohexene is replaced by 112 g. of 1-octene (1 mole). The reaction temperature is brought to 110° C. after which 0.07 mole of hydrogen peroxide is added in the form of a 70% aqueous solution. After two hours of reaction, the reaction medium is found to contain 0.016 mole of hydrogen peroxide and 0.047 mole of 1-octene epoxide. This corresponds to a conversion rate of $H_2O_2$ of 76% for a selectivity of 88.5%.

EXAMPLE 10

In a stainless steel piston reactor, 6 meters long with a diameter equal to 4 mm., kept at 90° C., there is injected under a pressure of 20 bars, with piston pumps at a rate of 245 g./hour, a solution of anhydrous hydrogen peroxide (0.125 mole/hour) and metaboric acid (0.114 mole/hour) in diglyme and 21 g./hour of propylene (0.5 mole). At the reactor outlet is collected a reaction mixture which, after cooling and degassing is subjected to analysis. A 31% conversion rate of hydrogen peroxide for a propylene oxide selectivity of 99%, was found by the analysis.

EXAMPLE 11

The procedure of Example 10 is repeated, except that the temperature is maintained at 110° C. A 99% conversion rate of hydrogen peroxide is obtained with a propylene oxide selectivity of 72%.

EXAMPLE 12

The procedure of Example 10 is repeated, except that the diglyme is replaced by dioxane. For a 41% hydrogen peroxide conversion rate, a propylene oxide selectivity of 99% is obtained.

EXAMPLE 13 (Comparison Test)

In a 300 ml. reactor equipped with a mechanical stirrer and a simple reflux condenser are placed 82 g. of cyclohexene (1 mole), 52 g. dioxane and 0.2 g. of boron trioxide $B_2O_3$ (0.003 mole), which is not a sufficient amount of catalyst to eliminate completely the water. The medium is brought to reflux at which time there is added over thirty minutes, a solution of 2.47 g. of 70% hydrogen peroxide (0.051 mole) in 20 g. of dioxane. The reaction mixture is kept boiling without distilling the water introduced with the hydrogen peroxide nor that formed during the reaction. After one hour of reaction, the reaction medium is found to contain 0.047 mole of unreacted hydrogen peroxide and 0.39 g. of cyclohexene epoxide which corresponds to a selectivity of 100% for a conversion rate of hydrogen peroxide of 7.8%.

It will be apparent from the foregoing that numerous variations and modifications will become obvious to those skilled in the art and, accordingly, the invention is not to be limited to the examples which have been disclosed.

What is claimed is:

1. A method of epoxidation of olefins by hydrogen peroxide at a temperature between 0° C. and 120° C. in a liquid phase which comprises, reacting an olefin and hydrogen peroxide in the presence of a catalyst selected from boron oxide or boron oxyacid catalysts, used in an amount of 0.0001 mole to 1 mole of catalyst per mole of hydrogen peroxide, continuously eliminating water introduced with the hydrogen peroxide as well as the water formed in the course of the reaction, from the reaction mixture by distillation during the course of the reaction, and recovering the epoxidized olefin.

2. A method according to claim 1 wherein the boron oxide is boron trioxide.

3. A method according to claim 1 wherein the boron oxyacid is metaboric acid, orthoboric acid or tetraboric acid.

4. A method according to claim 1 in which at least one organic solvent is included in the liquid phase, said solvent being inert with respect to the reactants and in which hydrogen peroxide is soluble under the reaction conditions.

5. A method according to claim 4 in which the organic solvent is a member of the group consisting of ethers, alcohols, polyols, esters.

6. A method according to claim 5 wherein the organic solvent is a member of the group consisting of oligomers of ethylene oxide, propylene oxide, corresponding methyl ethers, ethyl ethers and the formate, acetate or propionate species thereof.

7. A method according to claim 5 wherein the reaction is effected in the presence of diethylene glycol dimethyl ether as the solvent.

8. A method according to claim 5 wherein the reaction is effected in the presence of dioxane as the solvent.

9. A method according to claim 1 in which the olefin has the general formula:

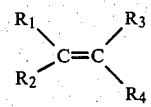

in which $R_1$, $R_2$, $R_3$ and $R_4$ are identical or different and represent either a hydrogen atom, a straight alkyl radical having from 1 to 30 carbon atoms, a branched alkyl radical or cycloalkyl radical, either substituted or unsubstituted and having from 3 to 12 carbon atoms, a hydrocarbon radical having from 6 to 12 carbon atoms and containing a phenyl group which may be substituted or unsubstituted by alkyl groups: $R_1$ and $R_2$ or $R_3$ and $R_4$ together may also represent a straight or branched alkylene group having from 2 to 11 carbon atoms or $R_1$ and $R_3$ or $R_2$ and $R_4$ together may represent a linear or branched alkylene group having from 1 to 10 carbon atoms: the radicals $R_1$, $R_2$, $R_3$ and $R_4$ can be unsaturated and/or substituted with functional groups which are stable in the reaction medium, such as hydroxy, chloro, fluoro, bromo, iodo, nitro, nitroso, alkoxy, amino, carbonyl, alkylcarbonyl, carboxylic acid, carboxylic acid ester, amide or carbamyl, nitrile or cyano.

10. A method according to claim 9 in which the olefin is propene.

11. A method according to claim 1 in which the reaction temperature is between 70° C. and 120° C.

12. A method according to claim 1 in which the pressure of reaction is between 20 mm. of Hg and 100 bars.

13. A method according to claim 1 in which the reactor contains 0.1 to 50 moles of olefins per mole of hydrogen peroxide.

14. A method according to claim 1 in which the hydrogen peroxide is in aqueous solution titrating between 70% to 95% by weight of hydrogen peroxide.

15. A method according to claim 1 in which the hydrogen peroxide is applied in organic solution titrating between 1% and 30% by weight of hydrogen peroxide.

* * * * *

UNITED STATES PATENT AND TRADEMARK OFFICE
CERTIFICATE OF CORRECTION

PATENT NO. : 4,303,587
DATED : December 1, 1981
INVENTOR(S) : Jean-Pierre Schirmann and Serge Y. Delavarenne It is certified that error appears in the above—identified patent and that said Letters Patent is hereby corrected as shown below:

Column 3, line 60, reads "3 to 11 carbon" should read --2 to 11 carbon--

Signed and Sealed this

Sixteenth Day of March 1982

[SEAL]

Attest:

GERALD J. MOSSINGHOFF

Attesting Officer    Commissioner of Patents and Trademarks